United States Patent [19]

Platzek et al.

[11] Patent Number: 5,730,956
[45] Date of Patent: Mar. 24, 1998

[54] DTPA DI-ALKYL MONOAMIDES FOR X-RAY AND MRI

[75] Inventors: Johannes Platzek; Ulrich Niedballa; Peter Mareski; Bernd Radüchel; Hanns-Joachim Weinmann, all of Berlin; Andreas Mühler, Neuenhagen; Bernd Misselwitz, Berlin, all of Germany

[73] Assignee: Schering Aktiengesellschaft, Berlin, Germany

[21] Appl. No.: 488,291

[22] Filed: Jun. 7, 1995

[30] Foreign Application Priority Data

Feb. 21, 1995 [DE] Germany ............ 195 07 819.5

[51] Int. Cl.$^6$ .................................... A61B 5/055
[52] U.S. Cl. ............ 424/9.365; 424/9.42; 514/836; 534/16; 556/50; 556/55; 556/63; 556/77; 556/105; 556/116; 556/134; 556/148
[58] Field of Search .................. 424/9.365, 9.42; 128/653.4, 654; 436/173; 514/492, 502, 836; 534/16; 556/50, 55, 63, 77, 105, 116, 134, 148

[56] References Cited

U.S. PATENT DOCUMENTS

| | | | |
|---|---|---|---|
| 4,859,451 | 8/1989 | Quay et al. | 424/9.365 |
| 5,011,925 | 4/1991 | Rajagopalan et al. | 544/58.1 |
| 5,087,439 | 2/1992 | Quay | 424/9.365 |
| 5,138,040 | 8/1992 | Moore et al. | 424/9.365 |
| 5,312,617 | 5/1994 | Unger et al. | 424/9.365 |
| 5,316,756 | 5/1994 | Gries et al. | 424/9.365 |
| 5,399,340 | 3/1995 | Radüchel et al. | 424/9 |
| 5,458,127 | 10/1995 | Unger et al. | 128/653.4 |
| 5,463,030 | 10/1995 | Subramanian et al. | 534/16 |
| 5,562,894 | 10/1996 | White | 424/9.365 |
| 5,571,498 | 11/1996 | Cacheris et al. | 424/9.365 |

OTHER PUBLICATIONS

Ma et al., "Use of the Gamma–Ray Perturbed Angular Correlation . . . ", *Pharmaceutical Research*, vol. 10, No. 2, 1993, pp. 252–257.

Hnatowich et al., "Labeling of Preformed Liposomes with Ga–67 and Tc–99m by Chelation", *J. Nucl. Med.* 22:810–814, 1981.

Gruaz–Guyon et al., "Radiolabeled hapten–derivatized peptides . . . ", *Peptides*, 1990, pp. 822–825.

Goto et al., "Effect of Reticuloendothelial Blockade on Tissue Distribution . . . ", *Chem. Pharm. Bull.*, 39(1) 230–232 (1991).

Steven et al., "Competitive Inhibition of a Tumour Cell Surface Protease . . . ", *J. Enzyme Inhib.*, 1990, vol. 4, pp. 63–73.

Maisano et al., "Coupling of DTPA to Proteins: A Critical Analysis . . . ", *Bioconjugate Chem.*, 1992, 3, 212–217.

Primary Examiner—Gary E. Hollinden
Attorney, Agent, or Firm—Millen, White, Zelano & Branigan, P.C.

[57] ABSTRACT

The invention relates to diethylenetriaminepentaacetic acid monoamide derivatives, their complexes and complex salts, containing gadolinium, dysprosium, iron or manganese, pharmaceutical agents containing these compounds, their use as contrast media and process for their production.

13 Claims, No Drawings

DTPA DI-ALKYL MONOAMIDES FOR X-RAY AND MRI

Invention relates to diethylenetriaminepentaacetic acid monoamide derivatives, their complexes and complex salts, pharmaceutical agents containing these compounds, their use as NMR contrast media and process for their production.

At the beginning of the 1950s, metal complexes were already considered as contrast media for radiology. But the compounds used at that time proved difficult to tolerate, so that a use in humans was not suitable. It was therefore very surprising that certain complex salts proved sufficiently compatible so that a routine use in humans could be taken into consideration.

In EP 71564 B1, i.a., the meglumine salt of the gadolinium(III) complex of diethylenetriaminepentaacetic acid (DTPA) is described as a contrast medium for NMR tomography. A preparation which contains this complex was approved worldwide under the name Magnevist® as the first NMR contrast medium. After intravenous administration, this contrast medium spreads extracellularly and is excreted renally by glomerular secretion. A passage of intact cell membranes is practically not observed. Magnevist® is especially well-suited for the visualization of pathological areas (e.g., inflammations, tumors).

But for the visualization of non-inflammatory and non-tumorous tissue parts, there is still a need for new contrast media, which exhibit a higher organ specificity or are excreted extrarenally.

For use as NMR contrast media, a number of DTPA derivatives with terminal amide linkages were proposed in patent specifications EP 0263051 A1, EP 0450742 A1 and EP 0413405 A1. But these compounds have not completely met the expectations, connected with their production, with respect to compatibility and pharmacokinetics.

In addition, in their clinical use, all previously known complexes and their salts cause problems with respect to compatibility and/or stability. The diagnostically valuable use of heavy elements as components of x-ray contrast media to be administered parenterally previously came to nothing with the insufficient compatibility of such compounds. The difference between the effective dose and the dose that is toxic in animal experiments is too small in the case of paramagnetic substances previously proposed or tested for nuclear spin tomography. They further exhibit an excessively small organ specificity. Moreover, their contrast-enhancing effect and their compatibility are insufficient in many cases.

Further, for many purposes, there is therefore a need particularly for better compatible, but also stable, readily soluble and sufficiently organ-specific complex compounds.

The object of the invention is thus to make available these compounds and agents as well as to provide a process for their production. The achievement of this object was performed by the object characterized in the claims.

It has been found that complexes which consist of the anion of a complexing monoamide of the central carboxylic acid of diethylenetriaminepentaacetic acid and a central ion of the elements of atomic numbers 20–29 or 57–83 and optionally one or more cations of an organic and/or inorganic base or amino acid are surprisingly excellently suited for the production of NMR and x-ray diagnostic agents.

The complexes according to the invention are described by general formula I

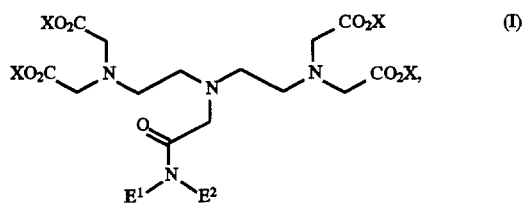

in which

X independently of one another, stand for a hydrogen atom or a metal ion equivalent of an element of atomic numbers 20–29 or 57–83, $E^1, E^2$ independently of one another, stand for a saturated or unsaturated, branched or straight-chain $C_1$–$C_{50}$ alkyl chain, in which the chain or parts of this chain optionally can form a cyclic $C_5$–$C_8$ unit or a bicyclic $C_{10}$–$C_{14}$ unit, which contains 0 to 10 oxygen and/or 0 to 2 sulfur atoms and/or 0 to 3 carbonyl, 0 to 1 thiocarbonyl, 0 to 2 imino, 0 to 2 phenylene, 0 to 13-indole, 0 to 1 methyl-imidazol-4-yl and/or 0 to 3N—$R^3$ groups, and are substituted by 0 to 2 phenyl, 0 to 2 pyridyl, 0 to 5 $R^2O$, to 1 HS, 0 to 4 $R^2OOC$, 0 to 4 $R^2OOC$—$C_{1-4}$ alkyl and/or 0 to 1 $R^2(H)N$ groups, in which optionally present aromatic groups can be substituted zero to five times, independently of one another, by fluorine, chlorine, bromine, iodine atoms, $R^2O_2C$, $R^2OOC$—$C_{1-4}$ alkyl, $C_{1-4}$ alkyl-NH, $R^2NHOC$, $R^2CONH$, $O_2N$, $R^2O$ and/or $R^2$ groups, $R^2$ independently of one another, stand for a hydrogen atom or a straight-chain or branched $C_1$–$C_4$ alkyl radical and $R^3$ independently of one another, stand for a hydrogen atom or a straight-chain or branched, saturated or unsaturated $C_1$–$C_{30}$ alkyl radical or $E^1$ and $E^2$, together with inclusion of the nitrogen atom, stand for a five- to eight-membered, saturated or unsaturated heterocycle, which optionally contains one to two additional nitrogen, oxygen, sulfur atoms and/or carbonyl groups, in which the HO and/or $H_2N$ and/or HS and/or HOOC group(s) optionally contained in $E^1$ and/or $E^2$ can be present in protected form and in which free carboxylic acid groups not used for complexing can also be present as salts with physiologically compatible inorganic and/or organic cations or as esters or amides.

The invention therefore relates to the complexes of general formula I, as described herein.

In particular, the invention relates to complexes of general formula I in which the central atom is gadolinium, dysprosium, iron or manganese, and $E^1$ and $E^2$, independently of one another, stand for hydrogen or for a saturated or unsaturated, straight-chain $C_1$–$C_{50}$ alkyl chain.

Further, the salts of the compounds of general formula I with organic and/or inorganic bases are numbered among the compounds according to the invention.

Compounds, which correspond to general formula I, but in which all occurring radicals X mean a hydrogen atom, are designated below as complexing agents; compounds of general formula I, in which at least two radicals X have the meaning of a metal ion equivalent, are designated as complexes. Salts of the complexes of general formula I, in which organic and/or inorganic bases act as counterion(s), are designated below as complex salts.

The designations of terminal or central carboxylic acid can be defined as follows:

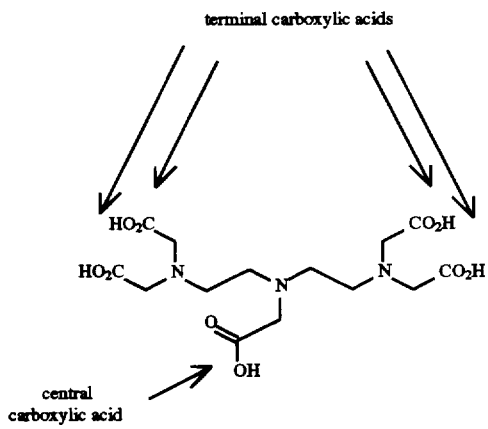

central carboxylic acid
terminal carboxylic acids

As groups $E^1$ or $E^2$, there can be mentioned as examples the hydrogen atom, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, cyclopentyl, cyclohexyl, cycloheptyl, cyclooctyl, cyclohexenyl, cyclopentanone, cyclohexanol, cyclohexenol, 2-aminocycloheptane, 2-hydroxyethyl, 5-oxononyl, hex-5-enyl, icosa-19-enyl, 2-ethylhexyl, 2-ethoxyhexyl, phenyl, benzyl, naphthyl, imidazolyl, thiazolyl radicals, as well as radicals of formulas:

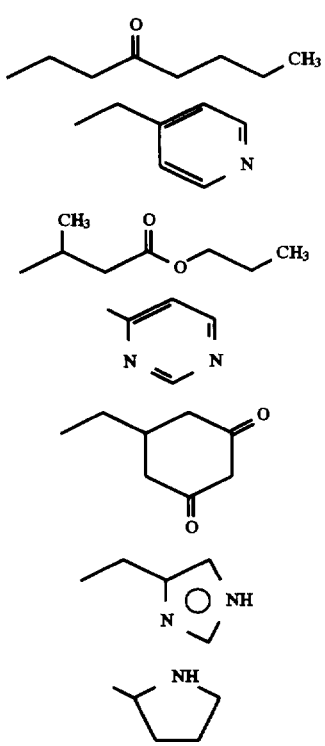

Preferred groups $E^1$ and $E^2$ are straight-chain alkyl radicals with up to 20 carbon atoms, hydrogen atoms, cyclohexyl, phenyl, benzyl, naphthyl radicals as well as radicals of general formula IV

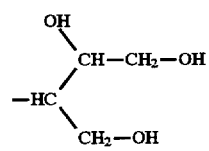

(IV)

as well as radicals of composition
—$(CH_2)_p$—$(G)_t$—$(CH_2)_q$COOH and
—$(CH_2)_p$—$(G)_t$—$(CH_2)_q$NH$_2$,
in which G stands for oxygen or sulfur, p,q independently of one another, stand for a number between 1 and 28, t stands for 0 or 1, and p+t+q≦30, the acid group can also be present as salt of an inorganic or organic base, as ester or as amide, or the amino group can also be present as ammonium salt with a physiologically compatible anion or as amide.

As groups in which $E^1$ and $E^2$, together with inclusion of the nitrogen atom, form a five- to eight-membered, saturated or unsaturated heterocycle, there can be mentioned as examples the imidazolyl, pyrazolyl, pyrrolyl, 3-pyrrolinyl, pyrrolidinyl, morpholinyl group or the piperidinyl group.

As radicals Z, there can be mentioned as examples methyl, ethyl, n-propyl, i-propyl, n-butyl, i-butyl, pentyl, hexyl, cyclohexyl radicals or phenyl or benzyl radicals, as well as radicals of formulas

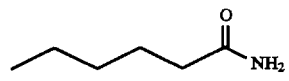

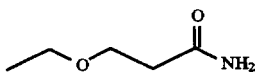

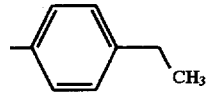

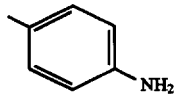

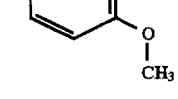

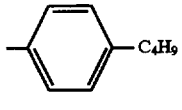

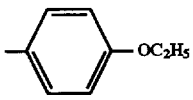

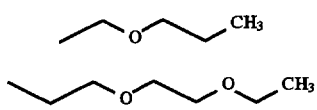

Production of the Complexes According to the Invention

The production of the complexes according to the invention takes place in the way in which it was disclosed in Patents EP 71564, EP 130934 and DE-OS 3401052, by the metal oxide or a metal salt (for example, a chloride, nitrate, acetate, carbonate or sulfate) of the element of atomic numbers 20–29 or 57–83 being dissolved or suspended in water and/or a lower alcohol (such as methanol, ethanol or isopropanol) and being reacted with the solution or suspension of the equivalent amount of the complexing agent of general formula I and then, if desired, existing acid hydrogen atoms of the acid groups being substituted by cations of inorganic and/or organic bases or amino acids.

In this case, the neutralization takes place with the help of inorganic bases (e.g., hydroxides, carbonates or bicarbonates) of, e.g., sodium, potassium, lithium, magnesium or calcium and/or organic bases, such as, i.a., primary, secondary and tertiary amines, such as, e.g., ethanolamine, glucamine, N-methyl and N,N-dimethyl-glucamine, as well as basic amino acids, such as, e.g., lysine, arginine and ornithine.

For the production of neutral complex compounds, enough of the desired bases can be added, for example, to the acid complex salts in aqueous solution or suspension so that the neutral point is reached. The resulting solution can then be evaporated to dryness in a vacuum. It is often advantageous to precipitate the neutral salts that are formed by adding water-miscible solvents, such as, e.g., lower alcohols (methanol, ethanol, isopropanol, etc.), lower ketones (acetone, etc.), polar ethers (tetrahydrofuran, dioxane, 1,2-dimethoxyethane, etc.) and thus to obtain easily isolated and readily purified crystallizates. It has proven especially advantageous to add the desired base as early as during the complexing of the reaction mixture and thus to save a process step.

If the acid complexes contain several free acid groups, it is often suitable to produce neutral mixed salts, which contain both inorganic and organic cations as counterions.

This can happen, for example, by the complexing agents being reacted in aqueous suspension or solution with the oxide or salt of the desired element and half of the amount of an organic base required for neutralization, the formed complex salt being isolated, optionally purified and then mixed with the required amount of inorganic base for complete neutralization. The sequence of the addition of base can also be reversed.

Another possibility to arrive at neutral complex compounds consists in converting the remaining acid groups, as described, e.g., in EP 0450742, completely or partially to esters or amides.

Production of the Complexing Agents According to the Invention

The production of the complexing agents of general formula I according to the invention takes place by cleavage of acid protective groups $R^1$ from compounds of general formula IV

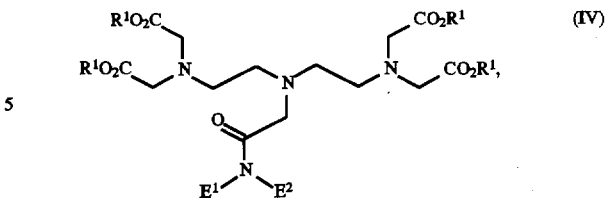

in which $R^1$ stands for a *tert*-butyl or a benzyl group and $E^1$ and $E^2$ have the above-indicated meaning.

The cleavage of the protective groups takes place according to the processes known to one skilled in the art, for example, by hydrolysis, hydrogenolysis, alkaline saponification of esters with alkali in aqueous-alcoholic solution at temperatures of 0° to 50° C., acid saponification with mineral acids or, in the case of *tert*-butyl esters, with the help of trifluoroacetic acid. Preferred are the hydrogenolytic cleavage of the benzyl group and the saponification of the *tert*-butyl group with trifluoroacetic acid.

The production of the compounds of general formula IV takes place in that compounds of general formula V

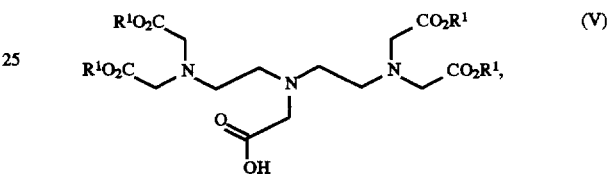

in which $R^1$ has the above-mentioned meaning, after activation of the free carboxylic acid group, are reacted with amines of general formula VI

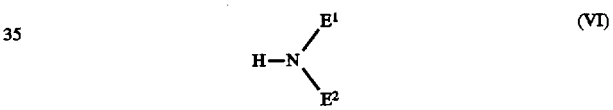

in the way known to one skilled in the art.

The linkage of compounds of general formula V with the amines of general formula VI takes place in organic solvents such as toluene or tetrahydrofuran at temperatures of −10° C. to 50° C., preferably room temperature and below, with addition of one or more activating reagents.

The activation can take place, for example, by reaction of acid with dicyclohexylcarbodiimide, N-hydroxysuccinimide/dicyclohexylcarbodiimide, carbonyldiimidazole, 2-ethoxy-1-ethoxycarbonyl-1,2-dihydroquinoline, oxalic acid dichloride or isobutyl chloroformate in the way described in the literature:

- ♦ Aktivierung von Carbonsäuren [Activation of Carboxylic Acids]. Übersicht in Houben-Weyl, Methoden der Organischen Chemie [Survey in Houben-Weyl, Methods of Organic Chemistry], Volume XV/2, Georg Thieme Verlag Stuttgart, 19.
- ♦ Aktivierung mit Carbodiimiden [Activation with Carbodiimides]. R. Schwyzer and H. Kappeler, Helv. 46:1550 (1963).
- ♦ E. Wünsch et al., B. 100:173 (1967).
- ♦ Aktivierung mit Carbodiimiden/Hydroxysuccinimid [Activation with Carbodiimides/Hydroxysuccinimide]: J. Am. Chem. Soc. 86:1839 (1964) as well as J. Org. Chem. 53:3583 (1988). Synthesis 453 (1972).
- ♦ Anhydridmethode, 2-Ethoxy-1-ethoxycarbonyl-1,2-dihydrochinolin [Anhydride Methods, 2-Ethoxy-1-ethoxycarbonyl-1,2-dihydroquinoline]: B. Belleau et al., J. Am. Chem. Soc., 90:1651 (1986), H. Kunz et al., Int. J. Pept. Prot. Res., 26:493 (1985) and J. R. Voughn, Am. Soc. 73:3547 (1951).

- ♦ Imidazolid-Methode [Imidazolide Methods]: B. F. Gisin, R. B. Menifield, D. C. Tosteon, Am. Soc. 91:2691 (1969).
- ♦ Säurechlorid-Methoden, Thionylchlorid [Acid Chloride Methods, Thionyl Chloride]: Helv., 42:1653 (1959).
- ♦ Oxalylchlorid [Oxalyl Chloride]: J. Org. Chem., 29:843 (1964).

Numerous amines, which correspond to general formula VI

in which $E^1$ and $E^2$ have the above-mentioned meanings, can be purchased (e.g.: E. Merck, Darmstadt, Fluka Chemie AG, CH-9470 Buchs) or can be produced as described, e.g., in Houben-Weyl, Methoden der organischen Chemie, Stickstoffverbindungen II [Nitrogen Compounds II], Volumes XI/1 and XI/2, Georg Thieme Verlag Stuttgart, 1957.

As amines of general formula VI, there can be mentioned as examples ammonia, methylamine, dimethylamine, ethylamine, diethylamine, n-propylamine, di-n-propylamine, hexylamine, di-n-hexylamine, n-nonylamine, di-n-nonylamine, icosamine, di-n-icosamine.

The production of compounds of general formula V takes place in that a feedstock of general formula VII

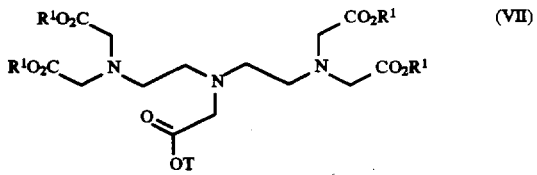

in which $R^1$ has the above-indicated meaning and can be a straight-chain or branched $C_1-C_6$ alkyl group, a benzyl, trimethylsilyl, triisopropylsilyl, 2,2,2-trifluoroethoxy, 2,2,2-trichloroethoxy group, or a metal ion equivalent of an alkali or alkaline-earth element, in which T is always different from $R^1$,
is converted by cleavage of group T to the compound of general formula V. Preferred radical T is the benzyl radical, if $R^1$ stands for a *tert*-butyl group.

The cleavage of protective group T from compounds of general formula VII takes place according to the processes known to one skilled in the art, such as, for example, by hydrolysis, hydrogenolysis, acid or alkaline saponification of esters in aqueous-alkaline medium, and optionally solubilizers such as alcohols, preferably methanol, ethanol, isopropanol or ethers, such as tetrahydrofuran, 1,4-dioxane, 1,2-dimethoxyethane, can be added. Alkali or alkaline-earth hydroxides (such as, e.g., lithium hydroxide, sodium hydroxide, barium hydroxide) or alkali or alkaline-earth carbonates (such as, e.g., potassium carbonate and cesium carbonate) can be used as bases. Preferred temperatures are 0°–100° C., especially 0°–50° C. The subsequent isolation of the compound of general formula V takes place so that it is reacted with an ammonium salt, such as, e.g., $NH_4Cl$, $(NH_4)_2SO_4$ or $(NH_4)_3PO_4$, or the salts are converted to the free acids with acid ion exchanger.

Also, the use of diluted citric or acid ion exchanger has proven itself for the release of the acid function from alkali or alkaline-earth salts. Silyl-containing protective groups are cleaved with fluoride ions.

The acid saponification is performed with mineral acids, such as, e.g., hydrochloric acid, sulfuric acid or else also organic acids (e.g., trifluoroacetic acid) at temperatures of 0°–100° C., preferably 0°–50° C., in the case of trifluoroacetic acid between 0°–25° C.

The hydrogenolytic cleavage of benzyl derivatives takes place with use of the palladium catalysts known to one skilled in the art, preferably 10% Pd on activated carbon or Pearlman's catalyst $Pd(OH)_2$ on carbon. Homogeneous catalysts of the Wilkinson catalyst type can also be used. The hydrogenation is performed in alcohols such as methanol, ethanol or isopropanol, but preferably in isopropanol, at temperatures between 10°–50° C., but preferably at room temperature and normal pressure.

The production of compounds of general formula VII takes place in that a glycine derivative of general formula VIII $$H_2N-CH_2-COOT \qquad \text{(VIII)}$$

in which T has the above-indicated meaning, is reacted with an alkylating reagent of general formula IX

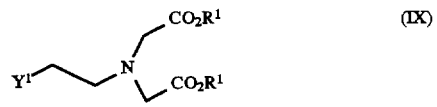

in which $R^1$ has the above-indicated meaning and $Y^1$ stands for a halogen atom such as Cl, Br or I, but preferably Cl (see also M. A. Williams, H. Rapoport, J. Org. Chem., 58, 1151 (1993)).

The reaction of compound (VIII) with compound (IX) takes place preferably in a buffered alkylation reaction, in which an aqueous phosphate buffer solution is used as buffer. The reaction takes place at pHs 7–9, but preferably at pH 8. The buffer concentration can be between 0.1–2.5M, but a 2M phosphate-buffer solution preferably is used. The temperature of the alkylation can be between 0° and 50° C., the preferred temperature is room temperature.

The reaction is performed in a polar solvent, such as, e.g., acetonitrile, tetrahydrofuran, 1,4-dioxane or 1,2-dimethoxyethane. Acetonitrile is preferably used.

If $Y^1$ in general formula IX is a chlorine or bromine atom, an alkali iodide, such as, e.g., sodium iodide or potassium iodide, can be added to the reaction in catalytic amounts.

The glycine esters of general formula VIII used in the reaction can be produced from the commercially available amino acids according to methods known to one skilled in the art (e.g., Houben-Weyl, Methoden der organischen Chemie, Synthese von Peptiden [Synthesis of Peptides], Part II, Volume XV/2, Georg Thieme Verlag Stuttgart, 1974, p. 3 ff). As commercially available products, amino acids and derivatives can be obtained, e.g., with the Fluka Chemie [Fluka Chemistry] AG, CH-9470 Buchs or the BACHEM Feinchemikalien [BACHEM Fine Chemicals] AG, CH-4416 Bubendorf.

Preferred glycine derivatives of general formula VIII are the glycine benzyl esters. In the synthesis of these compounds, salts (such as, e.g., hydrochlorides, hydrosulfates, sulfates, phosphates or p-toluene sulfonates) generally accumulate, which can be used advantageously directly in the reaction.

The structural element of general formula IX used in the alkylation can be produced analogously to the description of Rapoport if $Y^1$=Br. But the corresponding compound with $Y^1$=Cl can be used in the same way for the above-described reaction.

The chlorine compound can be produced economically, moreover, from the alcohol of general formula X

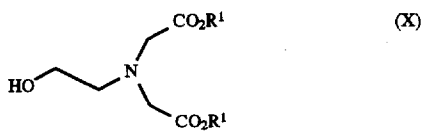

(X)

by reaction with thionyl chloride.

Production and Use of the Agents According to the Invention

The production of the pharmaceutical agents according to the invention takes place in a way known in the art, by the complex compounds according to the invention being suspended or dissolved in aqueous medium—optionally by adding the additives usual in galenicals—and then the suspension or solution optionally being sterilized. Suitable additives are, for example, physiologically harmless buffers (such as, for example, tromethamine), small additions of complexing agents (such as, for example, DTPA or the respective compounds of general formula I according to the invention with X meaning hydrogen) and/or their calcium, magnesium or zinc complexes or optionally electrolytes (such as, for example, sodium chloride) as well as antioxidants (such as, for example, ascorbic acid).

If suspensions or solutions of the agents according to the invention in water or physiological salt solution are desired for enteral administration or other purposes, they are mixed with one or more adjuvants usual in galenicals, such as, for example, methylcellulose, lactose or mannitol, and/or surfactants, such as, for example, lecithins, Tween® or Myrj®, and/or flavoring substances for taste correction, such as, for example, ethereal oils.

It is also possible to produce the pharmaceutical agents according to the invention without isolating the complex salts. In each case, special care must be used to undertake the chelation, so that the salts and salt solutions according to the invention are practically free of noncomplexed metal ions having a toxic effect.

This can be assured, for example, with the help of color indicators, such as xylenol orange, by control titrations during the production process. The invention therefore also relates to process for the production of complex compounds and their salts.

The pharmaceutical agents according to the invention preferably contain 1 μmol/1–2 mol/1 of the complex salt and are generally dosed in amounts of 0.001–20 mmol/kg of body weight. They are intended for enteral and parenteral administration.

The complex compounds according to the invention are used:

1. for NMR diagnosis in the form of their complexes with divalent and trivalent ions of the elements of atomic numbers 21–29 and 57–70. Suitable ions are, for example, the chromium(III), iron(II), cobalt(II), nickel (II), copper(II), praseodymium(III), neodymium(III), samarium(III) and ytterbium(III) ion. Because of their very strong magnetic moment, the gadolinium(III), terbium(III), dysprosium(III), holmium(III), erbium (III), manganese(II) and iron(III) ions are especially preferred.

2. for x-ray diagnosis in the form of their complexes with an element of a higher atomic number, which assures a sufficient absorption of x rays. It has been found that complexes according to the invention, which contain elements of atomic numbers 57–83 as central atom, are suitable for this application.

If X stands for one of the above-mentioned paramagnetic metals, the agents of general formula I according to the invention meet the varied requirements for suitability as contrast media for nuclear spin tomography. Thus, after oral or parenteral administration, they are excellently suited for improving the image, obtained with the help of the nuclear spin tomograph, in its informative value by increasing the signal intensity. Further, they show the high effectiveness that is necessary to load the body with the smallest possible amounts of foreign substances and the good compatibility, which is necessary to maintain the noninvasive nature of the examinations.

In general, the agents according to the invention for use as NMR diagnostic agents are dosed in amounts of 0.001–5 mmol/kg of body weight, preferably 0.005–0.5 mmol/kg of body weight. Details of the use are discussed, for example, in H. J. Weinmann et al., Am. J. of Roentgenology 142, 619 (1984).

Especially low dosages (under 1 mg/kg of body weight) of organ-specific NMR diagnostic agents can be used, for example, for detection of tumors and of myocardial infarction.

Further, the complex compounds according to the invention can advantageously be used as susceptibility reagents and as shift reagents for in vivo NMR spectroscopy.

In addition, the agents according to the invention are excellently suited as x-ray contrast media, and it is especially to be emphasized that no signs of the anaphylactic-type reactions in biochemical-pharmacological studies, known from the iodine-containing contrast media, can be detected with them. The substances according to the invention meet the varied requirements, which are imposed on contrast media in modern diagnosis. The compounds and agents produced from them are distinguished by a high absorption coefficient for x rays, a good compatibility, a high effectiveness, a low viscosity, a low osmolality, an advantageous precipitation kinetics.

In addition to the surprisingly good compatibility of the heavy metal complexes, the compounds according to the invention in x-ray diagnosis have a positive effect in that the complex compounds according to the invention especially also allow for studies with shorter-wave x-ray radiation than that which is possible with conventional contrast media, by which the radiation exposure of the patient is clearly reduced, since, as is generally known, soft radiation of tissue is much more greatly absorbed than hard [R. Felix, "Das Röntgenbild [The X-Ray Image]"; Thieme-Verlag Stuttgart (1980)].

Because of the advantageous absorption properties of the contrast media according to the invention in the area of hard x-ray radiation, the agents are also especially suitable for digital substraction techniques (which work with higher tube voltages).

Details of the use of x-ray contrast media are discussed, for example, in Barke, Röntgenkontrastmittel [X-Ray Contrast Media], G. Thieme, Leipzig (1970) and P. Thurn, E. Bücheler "Einführung in die Röntgendiagnostik [Introduction into X-Ray Diagnosis]," G. Thieme, Stuttgart, New York (1977).

In general, the agents according to the invention are dosed for use as x-ray contrast media in amounts of 0.1–20 mmol/kg of body weight, preferably 0.25–5 mmol/kg of body weight.

The agents according to the invention exhibit not only a high stability in vitro, but also a surprisingly high stability in vivo, so that a release or an exchange of ions—toxic in themselves—not covalently bound to the complexes does not take place within the time in which the new contrast media are completely excreted again.

The administration of aqueous x-ray and NMR contrast medium solutions can take place enterally or parenterally, namely orally, rectally, intravenously, intraarterially, intravascularly, intramuscularly, intracutaneously, subcutaneously or subarachnoidally (myelography) as a function of the diagnostic problem, and the intravenous administration is preferred.

The compounds according to the invention are especially suitable for lymphography. For this use of the compounds according to the invention, the administration can take place endolymphatically, interstitially or intravenously.

The uses of the compounds according to the invention in diagnosis are therefore also objects of the invention.

In general, it has been possible to synthesize new metal complexes and metal complex salts to open up new possibilities in diagnostic medicine.

The following examples are used for a more detailed explanation of the object of the invention without intending to be limited to this object.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding application(s) P 195 07 819.0, are hereby incorporated by reference.

EXAMPLES

Example 1

3,9-Bis(tert-butoxycarbonylmethyl)-3,6,9-triazaundecanedioic acid-di-tert-butyl ester a) 1,7-Bis(trifluoroacetyl)-1,4,7-triazaheptane 113.3 g (790 mmol) of trifluoroacetic acid ethyl ester is instilled in a solution of 41.14 g (390 mmol) of 1,4,7-triazaheptane in 350 ml of tetrahydrofuran at 0° C. and under nitrogen. It is allowed to stir overnight at room temperature, concentrated by evaporation in a vacuum. The remaining oil is crystallized from hexane.

Yield: 115 g (99.9% of theory)
Melting point: 68°–70° C.
Elementary analysis: Cld: C 32.55 H 3.76 F 38.62 N 14.24
Fnd: C 32.63 H 3.75 F 38.38 N 14.19 b) 1,7-Bis(trifluoroacetyl)-4-benzyloxycarbonyl-1,4,7-triazaheptane 14.75 g (50 mmol) of the trifluoroacetyl compound produced under Example 1a) as well as 8.3 ml (60 mmol) of triethylamine are dissolved in 120 ml of dichloromethane and cooled to 0° C. 7.5 ml (53 mmol) of benzyl chloroformate (97%), dissolved in 20 ml of dichloromethane, is now instilled with stirring. It is allowed to stir overnight at room temperature, the salts are extracted with distilled water, the dichloromethane solution is dried on sodium sulfate, evaporated to dryness in a vacuum and the residue is crystallized from ether/hexane.

Yield: 18.40 g (85.7% of theory)
Melting point: 131°–32° C.
Elementary analysis: Cld: C 44.76 H 3.99 F 26.55 N 9.79
Fnd: C 44.87 H 4.03 F 26.62 N 9.61 c) 3,9-Bis(tert-butoxycarbonylmethyl)-6-benzyloxycarbonyl-3,6,9-triazaundecanedicarboxylic acid-di-tert-butyl ester 4.29 g (10 mmol) of the trifluoroacetyl derivative produced under Example 1b) is dissolved in 30 ml of ethanol and mixed with 800 mg (20 mmol) of sodium hydroxide solution in 10 ml of distilled water. It is stirred for 3 hours at room temperature, evaporated to dryness in a vacuum at 40° C. bath temperature, water residues are removed by azeotropic distillation with isopropanol and taken up in 30 ml of dimethylformamide. Then, 6.9 g (50 mmol) of potassium carbonate as well as 9.7 g (50 mmol) of bromoacetic acid-tert-butyl ester are added to it and the 4-benzyloxycarbonyl-1,4,7-triazaheptane is alkylated at room temperature overnight. The dimethylformamide is then drawn off in an oil pump vacuum, the residue is dispersed between water and dichloromethane, the organic solution is dried on sodium sulfate, evaporated to dryness in a vacuum and the residue is purified by chromatography on silica gel. The title compound is eluted with ethyl acetate/hexane. It is obtained as foam.

Yield: 6.49 g (93.6% of theory)
Elementary analysis: Cld: C 62.32 H 8.57 N 6.06 Fnd: C 62.41 H 8.66 N 6.01 d) 3,9-Bis(tert-butoxycarbonylmethyl)-3,6,9-triazaundecanedicarboxylic acid-di-tert-butyl ester 3.5 g (5 mmol) of the compound produced under Example 1c) is dissolved in 100 ml of ethanol, mixed with 200 mg of Pearlman's catalyst (Pd 20% on activated carbon) and hydrogenated until the calculated amount of hydrogen is taken up. It is suctioned off from the catalyst and evaporated to dryness in a vacuum. The title compound is obtained as white foam.

Yield: 2.80 g (99.9% of theory)
Elementary analysis: Cld: C 60.08 H 9.54 N 7.51 Fnd: C 60.02 H 9.62 N 7.56

3,9-Bis(tert-butoxycarbonylmethyl)-6-carboxymethyl-3,6,9-triazaundecanedioic acid-di-tert-butyl ester e) 3,9-Bis(tert-butoxycarbonylmethyl)-6-benzyloxycarbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 2.58 g (12 mmol) of 2-bromoacetic acid benzyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 6.32 g (89.3% of theory)
Elementary analysis: Cld: C 64.65 H 9.00 N 5.95 Fnd: C 64.62 H 9.07 N 5.90 f) 3,9-Bis(tert-butoxycarbonylmethyl)-6-carboxy-methyl-3,6,9-triazaundecanedioic acid-di-tert-butyl ester 7.08 g (10 mmol) of the benzyl ester produced under 1e) is dissolved in 100 ml of ethanol and mixed with 0.4 g of Pearlman's catalyst (Pd 20%, C). It is hydrogenated until 224 ml of hydrogen is taken up, suctioned off from the catalyst, rewashed well with ethanol and the solution is evaporated to dryness in a vacuum. The product is obtained as foam, which crystallized from ether/hexane.

Yield: 6.87 g (97.3% of theory)
Melting point: 73°–75° C.
Elementary analysis: Cld: C 57.85 H 9.00 N 5.95 Fnd: C 57.91 H 9.11 N 6.01 g) 3,9-Bis(tert-butoxycarbonylmethyl)-6-(2-aminoethyl)-aminocarbonylmethyl-3,6,9-triazaundecanedioic acid-di-tert-butyl ester 5.00 g (8.09 mmol) of the title compound of Example 1f) is dissolved in 25 ml of dimethylformamide, and 1.02 g (8.90 mol) of N-hydroxysuccinimide is added. It is cooled off to 0° C. and 1.84 g (8.90 mmol) of dicyclohexylcarbodiimide is added. It is stirred for one hour at 0° C. and then for 4 hours at room temperature. It is cooled off to 0° C. and a solution of 2.67 g of 1.2 diaminoethane (44.5 mmol) in 50 ml of dimethylformamide is instilled within 10 minutes. It is stirred for one hour at 0° C., then overnight at room temperature. It is evaporated to dryness in a vacuum and the residue is taken up in 100 ml of ethyl acetate. It is filtered off from precipitated urea and the filtrate is washed twice with 100 ml each of 5% aqueous soda solution. The organic phase is dried on magnesium sulfate and evaporated to dryness in a vacuum. The residue is chromatographed on silica gel (mobile solvent: n-hexane/isopropanol 15:1). 2.83 g (53% of theory) of a colorless oil is obtained.

Elementary analysis: Cld: C 58.25 H 9.32 N 10.61 Fnd: C 58.17 H 9.25 N 10.55 h) 3,9-Bis(carboxymethyl)-6-(2-aminoethyl)-aminocarbonylmethyl-3,6,9-triazaundecanedioic acid 2.60 g (3.94 mmol) of the title compound of Example 1g) is dissolved in 100 ml of trifluoroacetic acid. It is stirred overnight at room temperature. It is evaporated to dryness in a vacuum, and the residue is chromatographed on silica gel (mobile solvent: ethanol/25% aqueous ammonia solution 20:1). The fractions containing the product are evaporated to dryness in a vacuum. The residue is dissolved in 100 ml of water. 15 ml of acid ion exchanger IR 120 (H⁺ form) is added and stirred for 10 minutes at room temperature. It is filtered off from the ion exchanger and evaporated to dryness in a vacuum.

Yield: 1.29 g (57% of theory) of a vitreous solid
Water content: 7.9%
Elementary analysis (relative to anhydrous substance):
Cld: C 44.13 H 6.71 N 16.08 Fnd: C 40.25 H 6.63 N 16.18 i) Gadolinium complex of 3,9-bis(carboxymethyl)-6-(2-aminoethyl)-aminocarbonylmethyl-3,6,9-triazaundecanedioic acid-monosodium salt 1.20 g (2.75 mmol) of the title compound of Example 1h) is dissolved with 15 ml of deionized water and mixed at room temperature in portions with 0.50 g (1.37 mmol) of gadolinium oxide. After a reaction time of 3 hours at 80° C., the now almost clear reaction solution is cooled off to room temperature and adjusted with 1N sodium hydroxide solution to pH 7.2. After filtration, the obtained filtrate is freeze-dried. Yield: 1.64 g (97.8% of theory) of an amorphous powder.

Water content: 7.93%
Elementary analysis (relative to anhydrous substance):
Cld: C 31.42 H 4.12 Gd 25.71 N 11.45 Na 3.76 Fnd: C 31.46 H 4.14 Gd 25.74 N 11.48 Na 3.80 j) Ytterbium complex of 3,9-bis(carboxymethyl)-6-(2-aminoethyl)-aminocarbonylmethyl-3,6,9-triazaundecanedioic acid-monosodium salt Analogously to Example 1i), after freeze-drying, the reaction of 1.0 g (2.29 mmol) of the title compound of Example 1h) with 0.45 g (1.15 mmol) of ytterbium oxide instead of gadolinium oxide yields 1.40 g (97.5% of theory) of the title compound as amorphous powder.

Water content: 8.06%
Elementary analysis (relative to anhydrous substance):
Cld: C 30.63 H 4.02 N 11.16 Na 3.66 Yb 27.58 Fnd: C 30.59 H 4.00 N 11.13 Na 3.61 Yb 27.51 k) Europium complex of 3,9-bis(carboxymethyl)-6-(2-aminoethyl)-aminocarbonylmethyl-3,6,9-triazaundecanedioic acid-monosodium salt Analogously to Example 1i), after freeze-drying, the reaction of 1.0 g (2.29 mmol) of the title compound of Example 1h) with 0.40 g (1.15 mmol) of europium oxide yields 1.36 g (98.0% of theory) of the title compound as amorphous powder.

Water content: 8.02%
Elementary analysis (relative to anhydrous substance):
Cld: C 31.69 H 4.16 N 11.55 Eu 25.06 Na 3.79 Fnd: C 31.66 H 4.10 N 11.51 Eu 25.01 Na 3.72

Example 2 a) 3,9-Bis(tert-butoxycarbonylmethyl)-6-(3-oxa-5-aminopentyl)-aminocarbonylmethyl-3,6,9-triazaundecanedioic acid-di-tert-butyl ester 5.00 g (8.09 mmol) of the title compound of Example 1f) is dissolved in 25 ml of dimethylformamide, and 1.02 g (8.90 mol) of N-hydroxysuccinimide is added. It is cooled off to 0° C. and 1.84 g (8.90 mmol) of dicyclohexylcarbodiimide is added. It is stirred for one hour at 0° C. and then for 4 hours at room temperature. It is cooled off to 0° C. and a solution of 2.67 g of 1.5 diamino-3-oxa-pentane (44.5 mmol) in 50 ml of dimethylformamide is instilled within 10 minutes. It is stirred for one hour at 0° C., then overnight at room temperature. It is evaporated to dryness in a vacuum and the residue is taken up in 100 ml of ethyl acetate. It is filtered off from precipitated urea and the filtrate is washed twice with 100 ml each of 5% aqueous soda solution. The organic phase is dried on magnesium sulfate and evaporated to dryness in a vacuum. The residue is chromatographed on silica gel (mobile solvent: n-hexane/ethyl acetate 20:1). 2.79 g (49% of theory) of a colorless oil is obtained.

Elementary analysis: Cld: C 58.01 H 9.31 N 9.95 Fnd: C 57.90 H 9.41 N 9.87 b) 3,9-Bis(carboxymethyl)-6-(3-oxa-5-aminopentyl)-aminocarbonylmethyl-3,6,9-triazaundecanedioic acid 2.60 g (3.69 mmol) of the title compound of Example 2a) is dissolved in 100 ml of trifluoroacetic acid. It is stirred overnight at room temperature. It is evaporated to dryness in a vacuum, and the residue is chromatographed on silica gel (mobile solvent: ethanol/25% aqueous ammonia solution 20:1). The fractions containing the product are evaporated to dryness in a vacuum. The residue is dissolved in 100 ml of water. 20 ml of acid ion exchanger IR 120 (H⁺ form) is added and stirred for 10 minutes at room temperature. It is filtered off from the ion exchanger and evaporated to dryness in a vacuum.

Yield: 1.11 g (57% of theory) of a vitreous solid
Water content: 8.9%
Elementary analysis: Cld: C 45.09 H 6.94 N 14.61 Fnd: C 45.17 H 6.86 N 14.55 c) Gadolinium complex of 3,9-bis(carboxymethyl)-6-(3-oxa-5-aminopentyl)-aminocarbonylmethyl-3,6,9-triazaundecanedioic acid-monosodium salt Analogously to Example 1i), after freeze-drying, the reaction of 2.4 g (5.00 mmol) of the title compound of Example 2b) with 0.90 g (2.50 mmol) of gadolinium oxide yields 3.23 g (98.6% of theory) of the title compound as amorphous powder.

Water content: 6.47%
Elementary analysis (relative to anhydrous substance):
Cld: C 32.97 H 4.46 N 10.68 Gd 23.98 Na 3.51 Fnd: C 32.91 H 4.44 N 10.63 Gd 23.92 Na 3.48 d) Dysprosium complex of 3,9-bis(carboxymethyl)-6-(3-oxa-5-aminopentyl)-aminocarbonylmethyl-3,6,9-triazaundecanedioic acid-monosodium salt Analogously to Example 1i), after freeze-drying, the reaction of 1.8 g (3.75 mmol) of the title compound of Example 2b) with 0.70 g (1.87 mmol) of dysprosium oxide instead of gadolinium oxide yields 2.40 g (96.8% of theory) of the title compound as amorphous powder.

Water content: 7.13%

Elementary analysis (relative to anhydrous substance): Cld: C 32.71 H 4.42 N 10.60 Dy 24.59 Na 3.48 Fnd: C 32.68 H 4.39 N 10.57 Dy 24.55 Na 3.41

Example 3 a) 3,9-Bis(tert-butoxycarbonylmethyl)-6-bis(octadecyl)-aminocarbonylmethyl-3,6,9-triazaundecanedioic acid-di-tert-butyl ester 5 g (8.09 mmol) of the title compound of Example 1f) and 4.22 g (8.09 mmol) of bis-octadecylamine are dissolved in 30 ml of toluene, and 2.20 g (8.9 mmol) of 2-ethoxy-1-ethoxycarbonyl-1,2-dihydroquinoline is added at 0° C. It is stirred for 30 minutes at 0° C., then overnight at room temperature. It is evaporated to dryness in a vacuum and the residue is chromatographed on silica gel (mobile solvent: hexane/ethyl acetate 20:10:1).

Yield: 7.99 g (88% of theory) of a colorless solid

Elementary analysis: Cld: C 70.67 H 11.50 N 4.99 Fnd: C 70.78 H 11.60 N 4.83 b) 3,9-Bis(carboxymethyl)-6-bis(octadecyl)-aminocarbonylmethyl-3,6,9-triazaundecanedioic acid 5 g (4.46 mmol) of the title compound of Example 3a) is dissolved in 100 ml of trifluoroacetic acid and stirred overnight at room temperature. It is evaporated to dryness in a vacuum and the residue is chromatographed on silica gel (mobile solvent: methylene chloride/ethanol/33% aqueous ammonia solution 20:5:0.5). The fractions containing the product are evaporated to dryness in a vacuum and the residue is dissolved in a mixture of 80 ml of ethanol/20 ml of water/30 ml of chloroform. 20 ml of acid ion exchanger IR 120 ($H^+$ form) is added and stirred for 30 minutes. It is filtered off from the ion exchanger and the filtrate is evaporated to dryness in a vacuum.

Yield: 2.67 g (65% of theory) of a glass-like solid

Water content: 2.7%

Elementary analysis: Cld: C 67.11 H 10.90 N 7.57 Fnd: C 67.21 H 10.98 N 7.46 c) Gadolinium complex of 3,9-bis(carboxymethyl)-6-bis(octadecyl)-amino-carbonylmethyl-3,6,9-triazaundecanedioic acid-monosodium salt 2.0 g (2.22 mmol) of the title compound of Example 3b) is dissolved in 100 ml of water/ethanol/chloroform (2:1:1)-mixture in boiling heat and mixed at 80° C. in portions with 0.40 g (1.11 mmol) of gadolinium oxide. Then, the thus obtained reaction solution is refluxed for 5 hours. After cooling off to room temperature, the solvent mixture is completely drawn off in a vacuum and the remaining residue is mixed with 200 ml of a water/n-butanol mixture (1:1). With vigorous stirring, pH 7.2 is set by mixing with 1N sodium hydroxide solution. After the separation of the butanol phase, the remaining aqueous phase is extracted completely with n-butanol. Then, the combined organic phases are evaporated to dryness in a vacuum.

Yield: 1.96 g (82.4% of theory) of a glass-like solid

Water content: 6.16%

Elementary analysis (relative to anhydrous substance): Cld: C 55.94 H 8.64 Gd 14.65 N 5.22 Na 2.14 Fnd: C 55.90 H 8.59 Gd 14.62 N 5.18 Na 2.11 d) Iron complex of 3,9-bis(carboxymethyl)-6-bis(octadecyl)-aminocarbonylmethyl-3,6,9-triazaundecanedioic acid-monosodium salt 1.0 g (1.11 mmol) of the title compound of Example 3b) is dissolved in 75 ml of water/ethanol/chloroform (2:1:1)-mixture in boiling heat and mixed at 80° C. in portions with 0.39 g (1.11 mmol) of iron(III)-acetylacetonate. Then, the thus obtained reaction solution is refluxed for 5 hours. After cooling off to room temperature, the solvent mixture is completely drawn off in a vacuum, and the remaining residue is mixed with 150 ml of a water/n-butanol mixture (1:1). With vigorous stirring, pH 7.2 is set by mixing with 1N sodium hydroxide solution. After the separation of the butanol phase, the remaining aqueous phase is extracted completely with n-butanol. Then, the combined, organic phases are evaporated to dryness in a vacuum.

Yield: 0.87 g (81.0% of theory) of a glass-like solid

Water content: 5.93%

Elementary analysis (relative to anhydrous substance): Cld: C 61.78 H 9.54 N 5.76 Fe 5.74 Na 2.36 Fnd: C 61.82 H 9.57 N 5.81 Fe 5.76 Na 2.41 e) Dysprosium complex of 3,9-bis(carboxymethyl)-6-bis(octadecyl)-aminocarbonylmethyl-3,6,9-triazaundecanedioic acid-monosodium salt 1.25 g (1.39 mmol) of the title compound of Example 3b) is dissolved in 75 ml of water/ethanol/chloroform (2:1:1)-mixture in boiling heat and mixed at 80° C. in portions with 0.26 g (0.69 mmol) of dysprosium oxide. Then, the thus obtained reaction solution is refluxed for 5 hours. After cooling off to room temperature, the solvent mixture is completely drawn off in a vacuum and the remaining residue is mixed with 150 ml of a water/n-butanol mixture (1:1). With vigorous stirring, pH 7.2 is set by mixing with 1N sodium hydroxide solution. After the separation of the butanol phase, the remaining aqueous phase is extracted completely with n-butanol. Then, the combined, organic phases are evaporated to dryness in a vacuum.

Yield: 1.34 g (89.6% of theory) of a glass-like solid

Water content: 5.85%

Elementary analysis (relative to anhydrous substance): Cld: C 55.67 H 8.60 Dy 15.06 N 5.19 Na 2.13 Fnd: C 55.61 H 8.76 Dy 15.02 N 5.16 Na 2.10 f) Manganese complex of 3,9-bis(carboxymethyl)-6-bis(octadecyl)-amino-carbonylmethyl-3,6,9-triazaundecanedioic acid-disodium salt 2.0 g (2.22 mmol) of the title compound of Example 3b) is dissolved in 150 ml of water/ethanol/chloroform (2:1:1)-mixture in boiling heat and mixed at 80° C. in portions with 0.25 g (2.22 mmol) of manganese(II)-carbonate. Then, the thus obtained reaction solution is refluxed for 5 hours. After cooling off to room temperature, the solvent mixture is completely drawn off in a vacuum and the remaining residue is mixed with 200 ml of a water/n-butanol mixture (1:1). With vigorous stirring, pH 7.2 is set by mixing with 1N sodium hydroxide solution. After the separation of the butanol phase, the remaining aqueous phase is extracted completely with n-butanol. Then, the combined organic phases are evaporated to dryness in a vacuum.

Yield: 1.86 g (84.2% of theory) of a glass-like solid

Water content: 5.79%

Elementary analysis (relative to anhydrous substance): Cld: C 60.40 H 9.33 Mn 5.53 N 5.64 Na 4.62 Fnd: C 60.33 H 9.29 Mn 5.51 N 5.60 Na 4.59

Example 4 a) Bis(octadecyl)-aminoacetic acid 30 g (57.47 mmol) of bis-octadecylamine and 8.38 g (60.3 mmol) of bromoacetic acid are dissolved in a mixture of 150 ml of toluene/10 ml of dioxane and refluxed overnight. 200 ml of 5% aqueous ammonia solution is added and stirred for 10 minutes. The organic phase is separated, dried on magnesium sulfate and evaporated to dryness in a vacuum. The residue is chromatographed on silica gel (mobile solvent: methylene chloride/ethanol=20:1).

Yield: 20.33 g (61% of theory) of a waxy solid

Elementary analysis: Cld: C 78.69 H 13.38 N 2.41 Fnd: C 78.80 H 13.50 N 2.34 b) 1-[Bis(octadecyl)amino]-2-oxo-3-aza-13-aminotridecane 10 g (17.24 mmol) of the title compound of Example 4a) and 2.18 g (18.96 mmol) of N-hydroxysuccinimide are dissolved in 100 ml of dimethylformamide. It is cooled to 0° C. and 3.91 g (18.96 mmol) of dicyclohexylcarbodiimide is added. It is stirred for 1 hour at 0° C., then for 3 hours at room temperature. It is filtered off from precipitated urea and the filtrate is instilled within 30 minutes in a solution of 9.80 g (56.88 mmol) of diaminodecane and 5.76 g (56.88 mmol) of triethylamine in 200 ml of methylene chloride. It is stirred overnight at room temperature. It is evaporated to dryness in a vacuum, and the residue is dissolved in 200 ml of toluene. The organic phase is washed twice with 100 ml each of 5% aqueous soda solution, dried on magnesium sulfate and evaporated to dryness in a vacuum. The residue is chromatographed on silica gel (mobile solvent: methylene chloride/isopropanol/triethylamine=50:2:1).

Yield: 5.19 g (41% of theory) of a waxy solid

Elementary analysis: Cld: C 78.51 H 13.59 N 5.72 Fnd: C 78.61 H 13.68 N 5.60 c) 3,9-Bis(tert-butoxycarbonylmethyl)-6-[11-aza-13-bis(octadecyl)amino-12-oxo-tridecyl]aminocarbonylmethyl-3,6,9-triazaundecanedioic acid-di-tert-butyl ester 5 g (8.09 mmol) of the title compound of Example 1f) is dissolved in 25 ml of dimethylformamide, and 1.44 g (8.9 mmol) of N,N'-carbonyldiimidazole is added. It is stirred for 4 hours at room temperature. The solution is cooled off to 0° C., and a solution of 5.94 g (8.09 mmol) of the title compound of Example 4b) and 0.82 g (8.09 mmol) of triethylamine, dissolved in 50 ml of methylene chloride, is instilled within 30 minutes. It is stirred overnight at room temperature. It is evaporated to dryness, the residue is taken up in 150 mol of toluene and extracted twice with 100 ml each of 5% aqueous soda solution. The organic phase is dried on magnesium sulfate and concentrated by evaporation in a vacuum. The residue is chromatographed on silica gel (mobile solvent: methylene chloride/hexane/acetone=20:10:1).

Yield: 8.42 g (78% of theory) of a waxy solid

Elementary analysis: Cld: C 70.22 H 11.48 N 6.30 Fnd: C 70.31 H 11.59 N 6.17 d) 3,9-Bis(carboxymethyl)-6-[11-aza-13-bis(octadecyl)amino-12-oxo-tridecyl]aminocarbonylmethyl-3,6,9-triazaundecanedioic acid 5 g (3.75 mmol) of the title compound of Example 4c) is dissolved in 100 ml of trifluoroacetic acid and stirred overnight at room temperature. It is evaporated to dryness in a vacuum, and the residue is chromatographed on silica gel (mobile solvent: methylene chloride/ethanol/33% aqueous ammonia solution 20:5:0.5). The fractions containing the product are evaporated to dryness in a vacuum and the residue is dissolved in a mixture of 80 ml of ethanol/20 ml of water/30 ml of chloroform. 15 ml of acid ion exchanger IR 120 (H$^+$ form) is added and stirred for 30 minutes. It is filtered off from the ion exchanger and the filtrate is evaporated to dryness in a vacuum.

Yield: 3.05 g (71% of theory) of a glass-like solid

Water content: 3.1%

Elementary analysis: Cld: C 67.11 H 10.90 N 7.57 Fnd: C 67.21 H 10.98 N 7.46 e) Gadolinium complex of 3,9-bis(carboxymethyl)-6-[11-aza-13-bis(octadecyl)amino-12-oxo-tridecyl]aminocarbonylmethyl-3,6,9-triazaundecanedioic acid-monosodium salt 2.5 g (2.25 mmol) of the title compound of Example 4d) is dissolved in 150 ml of water/ethanol/chloroform (2:1:1)-mixture in boiling heat and mixed at 80° C. in portions with 0.40 g (1.12 mmol) of gadolinium oxide. Then, the thus obtained reaction solution is refluxed for 5 hours. After cooling off to room temperature, the solvent mixture is completely drawn off in a vacuum and the remaining residue is mixed with 250 ml of a water/n-butanol mixture (1:1). With vigorous stirring, pH 7.2 is set by mixing with 1N sodium hydroxide solution. After the separation of the butanol phase, the remaining aqueous phase is extracted completely with n-butanol. Then, the combined, organic phases are evaporated to dryness in a vacuum.

Yield: 2.67 g (92.4% of theory) of a glass-like solid

Water content: 6.31%

Elementary analysis (relative to anhydrous substance): Cld: C 57.91 H 9.09 Gd 12.23 N 6.54 Na 1.79 Fnd: C 57.87 H 9.02 Gd 12.20 N 6.52 Na 1.77 f) Manganese complex of 3,9-bis(carboxymethyl)-6-[11-aza-13-bis(octadecyl)amino-12-oxo-tridecyl]aminocarbonylmethyl-3,6,9-triazaundecanedioic acid-disodium salt 1.5 g (1.35 mmol) of the title compound of Example 4d) is dissolved in 100 ml of water/ethanol/chloroform (2:1:1)-mixture in boiling heat and mixed at 80° C. in portions with 0.15 g (1.35 mmol) of manganese (II)-carbonate. Then, the thus obtained reaction solution is refluxed for 5 hours. After cooling off to room temperature, the solvent mixture is completely drawn off in a vacuum and the remaining residue is mixed with 150 ml of a water/n-butanol mixture (1:1). With vigorous stirring, pH 7.2 is set by mixing with 1N sodium hydroxide solution. After the separation of the butanol phase, the remaining aqueous phase is extracted completely with n-butanol. Then, the combined, organic phases are evaporated to dryness in a vacuum.

Yield: 1.38 g (85.1% of theory) of a glass-like solid

Water content: 7.02%

Elementary analysis (relative to anhydrous substance): Cld: C 61.72 H 9.69 N 6.97 Mn 4.55 Na 3.81 Fnd: C 61.68 H 9.67 N 6.94 Mn 4.50 Na 3.78

Example 5 a) 3,9-Bis(tert-butoxycarbonylmethyl)-6-[3-aza-4-oxo-heneicosyl)-aminocarbonylmethyl-3,6,9-triazaundecanedioic acid-di-tert-butyl ester 5 g (7.58 mmol) of the title compound of Example 1g) and 2.30 g (22.73 mmol) of triethylamine are dissolved in 40 ml of methylene chloride. At 0° C., a solution of 2.53 g (8.34 mmol) of octadecanoic acid chloride in 20 ml of methylene chloride is instilled within 20 minutes. It is stirred overnight at room temperature. It is extracted with 50 ml of 5% aqueous salt solution, the organic phase is dried on magnesium sulfate and evaporated to dryness. The residue is chromatographed on silica gel (mobile solvent: methylene chloride/hexane/isopropanol=20:10:1).

Yield: 6.39 g (91% of theory) of a waxy solid

Elementary analysis: Cld: C 64.83 H 10.34 N 7.56 Fnd: C 64.73 H 10.40 N 7.48 b) 3,9-Bis(carboxymethyl)-6-[3-aza-4-oxo-heneicosyl)-aminocarbonylmethyl-3,6,9-triazaundecanedioic acid 5 g (5.4 mmol) of the title compound of Example 5a) is dissolved in 100 ml of trifluoroacetic acid and stirred overnight at room temperature. It is evaporated to dryness in a vacuum and the residue is chromatographed on silica gel (mobile solvent: methylene chloride/ethanol/33% aqueous ammonia solution 20:5:0.5). The fractions containing the product are evaporated to dryness in a vacuum, and the residue is dissolved in a mixture of 80 ml of ethanol/20 ml of water/30 ml of chloroform. 15 ml of acid ion exchanger IR 120 ($H^+$ form) is added and stirred for 30 minutes. It is filtered off from the ion exchanger, and the filtrate is evaporated to dryness in a vacuum.

Yield: 2.51 g (64% of theory) of a glass-like solid
Water content: 3.5%

Elementary analysis (relative to anhydrous substance):
Cld: C 58.18 H 9.05 N 9.98 Fnd: C 58.03 H 9.14 N 9.89 c) Gadolinium complex of 3,9-bis(carboxymethyl)-6-[3-aza-4-oxo-heneicosyl)-aminocarbonylmethyl-3,6,9-triazaundecanedioic acid-monosodium salt 2.0 g (2.85 mmol) of the title compound of Example 5b) is dissolved in 150 ml of water/ethanol/chloroform (2:1:1) -mixture in boiling heat and mixed at 80° C. in portions with 0.51 g (1.42 mmol) of gadolinium oxide. Then, the thus obtained reaction solution is refluxed for 5 hours. After cooling off to room temperature, the solvent mixture is completely drawn off in a vacuum, and the remaining residue is mixed with 250 ml of a water/n-butanol mixture (1:1). With vigorous stirring, pH 7.2 is set by mixing with 1N sodium hydroxide solution. After the separation of the butanol phase, the remaining aqueous phase is extracted completely with n-butanol. Then, the combined, organic phases are evaporated to dryness in a vacuum.

Yield: 2.06 g (82.6% of theory) of a glass-like solid
Water content: 7.66%

Elementary analysis (relative to anhydrous substance):
Cld: C 46.51 H 6.77 Gd 17.91 N 7.98 Na 2.62 Fnd: C 46.48 H 6.73 Gd 17.88 N 7.95 Na 2.59 d) Manganese complex of 3,9-bis(carboxymethyl)-6-[3-aza-4-oxo-heneicosyl)-aminocarbonylmethyl-3,6,9-triazaundecanedioic acid-disodium salt 1.5 g (2.13 mmol) of the title compound of Example 5b) is dissolved in 100 ml of water/ethanol/chloroform (2:1:1) -mixture in boiling heat and mixed at 80° C. in portions with 0.24 g (2.13 mmol) of manganese(II)-carbonate. Then, the thus obtained reaction solution is refluxed for 5 hours. After cooling off to room temperature, the solvent mixture is completely drawn off in a vacuum, and the remaining residue is mixed with 200 ml of a water/n-butanol mixture (1:1). With vigorous stirring, pH 7.2 is set by mixing with 1N sodium hydroxide solution. After the separation of the butanol phase, the remaining aqueous phase is extracted completely with n-butanol. Then, the combined, organic phases are evaporated to dryness in a vacuum.

Yield: 1.50 g (88.6% of theory) of a glass-like solid
Water content: 6.41%

Elementary analysis: Cld: C 51.12 H 7.45 Mn 6.88 N 8.77 Na 5.76 Fnd: C 51.08 H 7.40 Mn 6.84 N 8.74 Na 5.73

Example 6 a) 3,9-Bis(tert-butoxycarbonylmethyl)-6-(10-carboxydecyl) -aminocarbonylmethyl-3,6,9-triazaundecanedioic acid-di-tert-butyl ester 5 g (8.09 mmol) of the title compound of Example 1f) and 0.82 g (8.09 mmol) of triethylamine are dissolved in 50 ml of methylene chloride. At −10° C., a solution of 1.10 g (8.09 mmol) of isobutyl chloroformate in 20 ml of methylene chloride is instilled within 5 minutes and stirred for 20 minutes at −10° C. The solution is cooled to 15° C., and a solution of 1.63 g (8.09 mmol) of 11-aminoundecanoic acid and 2.43 g (24 mmol) of triethylamine in 50 ml of methylene chloride is instilled within 10 minutes and stirred for 30 minutes at −15° C., then overnight at room temperature. It is extracted twice with 100 ml each of 10% aqueous ammonium chloride solution, the organic phase is dried on magnesium sulfate and evaporated to dryness in a vacuum. The residue is chromatographed on silica gel (mobile solvent: methylene chloride/ethanol=20:1).

Yield: 4.41 g (68% of theory) of a colorless solid
Elementary analysis: Cld: C 61.47 H 9.56 N 6.99 Fnd: C 61.53 H 9.48 N 6.89 b) 3,9-Bis(carboxymethyl)-6-(10-carboxydecyl)-aminocarbonylmethyl-3,6,9-triazaundecanedioic acid 4 g (4.99 mmol) of the title compound of Example 6a) is dissolved in 100 ml of trifluoroacetic acid. It is stirred overnight at room temperature. It is evaporated to dryness in a vacuum, and the residue is chromatographed on silica gel (mobile solvent: ethanol/25% aqueous ammonia solution 20:1). The fractions containing the product are evaporated to dryness in a vacuum. The residue is dissolved in 100 ml of water. 16 ml of acid ion exchanger IR 120 ($H^+$ form) is added and stirred for 10 minutes at room temperature. It is filtered off from the ion exchanger and evaporated to dryness in a vacuum.

Yield: 1.95 g (63% of theory) of a vitreous solid
Water content: 6.8%

Elementary analysis (relative to anhydrous substance):
Cld: C 52.07 H 7.69 N 9.72 Fnd: C 52.15 H 7.60 N 9.64 c) Gadolinium complex of 3,9-bis(carboxymethyl)-6-(10-carboxydecyl)-aminocarbonylmethyl-3,6,9-triazaundecanedioic acid-disodium salt 2.0 g (3.46 mmol) of the title compound of Example 6b) is suspended in 150 ml of deionized water and mixed at 80° C. in portions with 0.62 g (1.73 mmol) of gadolinium oxide. After a reaction time of 3 hours at 80° C., the now almost clear reaction solution is cooled off to room temperature, and pH 7.2 is set with 1N sodium hydroxide solution. After filtration, the obtained filtrate is freeze-dried.

Yield: 2.33 g (87.2% of theory) of an amorphous powder
Water content: 8.13%

Elementary analysis (relative to anhydrous substance):
Cld: C 38.75 H 5.07 Gd 20.29 N 7.23 Na 5.93 Fnd: C 38.72 H 5.01 Gd 20.26 N 7.20 Na 5.89 d) Manganese complex of 3,9-bis(carboxymethyl)-6-(10-carboxydecyl)-aminocarbonylmethyl-3,6,9-triazaundecanedioic acid-trisodium salt 1.0 g (1.73 mmol) of the title compound of Example 6b) is suspended in 100 ml of deionized water and mixed at 80° C. in portions with 0.20 g (1.73 mmol) of manganese(II) carbonate. After a reaction time of 3 hours at 80° C., the now almost clear reaction solution is cooled off to room temperature, and pH 7.2 is set with 1N sodium hydroxide solution. After filtration, the obtained filtrate is freeze-dried.

Yield: 1.06 g (88.4% of theory) of an amorphous powder
Water content: 8.83%

Elementary analysis (relative to anhydrous substance):
Cld: C 43.17 H 5.65 Mn 7.90 N 8.06 Na 9.92 Fnd: C 43.14 H 5.60 Mn 7.86 N 8.01 Na 9.88 e) Iron complex of 3,9-bis(carboxymethyl)-6-(10-carboxydecyl)-aminocarbonylmethyl-3,6,9-triazaundecanedioic acid-disodium salt 1.0 g (1.73 mmol) of the title compound of Example 6b) is suspended in 100 ml of deionized water and mixed at 80° C. in portions with 0.61 g (1.73 mmol) of iron(III)-acetylacetonate. After a reaction time of 3 hours at 80° C., the now almost clear reaction solution is cooled off to room temperature, extracted twice with methylene chloride, and pH 7.2 is set with 1N sodium hydroxide solution. After filtration, the obtained filtrate is freeze-dried.

Yield: 1.04 g (89.2% of theory) of an amorphous powder
Water content: 8.11%

Elementary analysis (relative to anhydrous substance):
Cld: C 44.59 H 5.84 Fe 8.29 N 8.32 Na 6.83 Fnd: C 44.57 H 5.81 Fe 8.27 N 8.30 Na 6.80

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:
1. Compounds of general formula I

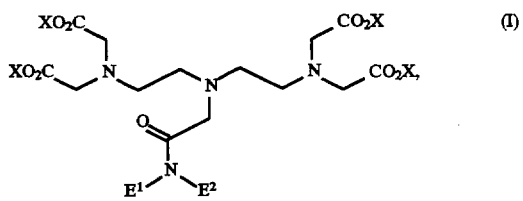

in which

X independently of one another, stand for a hydrogen atom or a metal ion equivalent of an element of atomic numbers 20–29 or 57–83, $E^1$, E2 independently of one another, stand for a saturated or unsaturated, branched or straight-chain $C_{10}$–$C_{50}$ alkyl chain, in which the chain or parts of this chain optionally can form a cyclic $C_5$–$C_8$ unit or a bicyclic $C_{10}$–$C_{14}$ unit, which contains 0 to 10 oxygen and/or 0 to 2 sulfur atoms and/or 0 to 3 carbonyl, 0 to 1 thiocarbonyl, 0 to 2 imino, 0 to 2 phenylene, 0 to 1 3-indole, 0 to 1 methyl-imidazol-4-yl and/or 0 to 3 N—$R^3$ groups, and are substituted by 0 to 2 phenyl, 0 to 2 pyridyl, 0 to 5 $R^2O$, 0 to 1 HS, 0 to 4 $R^2OOC$, 0 to 4 $R^2OOC$—$C_{1-4}$ alkyl and/or 0 to 1 $R^2(H)N$ groups, in which optionally present aromatic groups can be substituted zero to five times, independently of one another, by fluorine, chlorine, bromine, iodine atoms, $R^2O_2C$, $R^2OOC$—$C_{1-4}$ alkyl, $C_{1-4}$ alkyl-NH, $R^2NHOC$, $R^2CONH$, $O_2N$, $R^2O$ and/or $R^2$ groups, $R^2$ independently of one another, stand for a hydrogen atom or a straight-chain or branched $C_1$–$C_4$ alkyl radical and $R^3$ independently of one another, stand for a hydrogen atom or a straight-chain or branched, saturated or unsaturated $C_1$–$C_{30}$ alkyl radical in which the HO and/or $H_2N$ and/or HS and/or HOOC group(s) optionally contained in $E^1$ and/or $E^2$ can he present in protected form and in which free carboxylic acid groups not used for complexing can also be present as salts with physiologically compatible inorganic and/or organic cations or as esters or amides.

2. Complexes according to claim 1, characterized in that the central atom is gadolinium, dysprosium, iron or manganese and $E^1$ and $E^2$, independently of one another, stand for a saturated or unsaturated, straight-chain $C_{10}$–$C_{50}$ alkyl chain.

3. Complexes according to claim 1, wherein at least one of radicals $E^1$ and $E^2$ stands for a straight-chain $C_{10}$–$C_{50}$ alkyl chain, which is interrupted by 1 to 10 oxygen atoms.

4. Compounds according to claim 1, wherein at least one of radicals $E^1$ and $E^2$ stands for a radical of at least 10 carbon atoms of the formula

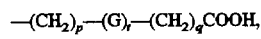

in which

G stands for oxygen or sulfur, p,q independently of one another, stand for a number between 1 and 28, t stands for 0 or 1, and p+t+q≦30, the acid group can also be present as salt of an inorganic or organic base, as ester or as amide.

5. Compounds according to claim 1, wherein at least one of radicals $E^1$ and $E^2$ stands for a radical of at least 10 carbon atoms of the formula

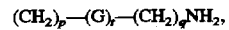

in which

G stands for oxygen or sulfur, p,q independently of one another, stand for a number between 1 and 28, t stands for 0 or 1, and p+t+q≦30, and the amino group can also be present as ammonium salt with a physiologically compatible anion of an inorganic or organic acid.

6. Complexes according to claim 1, wherein the central atom is gadolinium, europium, terbium, dysprosium or bismuth.

7. Complexes according to claim 1, wherein the central atom is iron or manganese.

8. Complexes according to claim 1, wherein at least one of radicals $E^1$ and $E^2$ stands for n-decyl, n-undecyl, n-dodecyl, n-tridecyl, n-tetradecyl, n-pentadecyl, n-hexadecyl, n-heptadecyl, n-octadecyl, n-nonadecyl, or n-icosyl radical.

9. Complexes according to claim 1, wherein at least one of radicals $E^1$ and $E^2$ stands for a straight-chained alkyl radical with 21 to 50 carbon atoms.

10. Pharmaceutical agents containing at least one physiologically compatible compound according to claim 1, optionally with the additives usual in galenicals.

11. A method of using a physiologically compatible compound according to claim 1 which comprises producing an agent for NMR diagnosis with the physiologically compatible compound according to claim 1.

12. A method of using a physiologically compatible compound according to claim 1 which comprises producing an agent for X-ray diagnosis with a physiologically compatible compound according to claim 1.

13. A method of using a physiologically compatible compound according to claim 1 which comprises producing an agent for lymphography with a physiologically compatible compound according to claim 1.

* * * * *